United States Patent
Miyake et al.

(10) Patent No.: US 10,882,806 B2
(45) Date of Patent: Jan. 5, 2021

(54) PROCESSES FOR PREPARING 4-METHYL-5-NONANONE AND 4-METHYL-5-NONANOL

(71) Applicant: Shin-Etsu Chemical Co., Ltd., Tokyo (JP)

(72) Inventors: Yuki Miyake, Niigata (JP); Takeshi Kinsho, Niigata (JP); Ryo Komatsu, Niigata (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 16/722,138

(22) Filed: Dec. 20, 2019

(65) Prior Publication Data
US 2020/0199053 A1    Jun. 25, 2020

(30) Foreign Application Priority Data
Dec. 21, 2018 (JP) ................. 2018-239546

(51) Int. Cl.
C07C 29/143    (2006.01)
C07C 17/16     (2006.01)
C07C 51/56     (2006.01)
C07C 45/45     (2006.01)
C07C 51/487    (2006.01)

(52) U.S. Cl.
CPC ............ C07C 29/143 (2013.01); C07C 17/16 (2013.01); C07C 45/455 (2013.01); C07C 51/56 (2013.01); C07C 51/487 (2013.01)

(58) Field of Classification Search
CPC ... C07C 29/143; C07C 45/676; C07C 17/013; C07C 9/18; C07C 51/487; C07C 45/455; C07C 17/16
See application file for complete search history.

(56) References Cited

U.S. PATENT DOCUMENTS

| | | | | |
|---|---|---|---|---|
| 6,864,394 B2 * | 3/2005 | Goossen | ................. | C07C 45/45 568/311 |
| 7,175,784 B2 * | 2/2007 | Weiss | ........................ | C07F 1/02 260/665 R |
| 10,392,325 B2 * | 8/2019 | Kurihara | ................... | B01D 3/10 |

FOREIGN PATENT DOCUMENTS

| | | | | |
|---|---|---|---|---|
| CN | 1117052 | * | 8/2003 | ........... C07C 29/145 |
| IN | 20150490514 | | 3/2017 | |
| JP | 2526963 B2 | * | 8/1996 | ............. C07B 61/00 |

OTHER PUBLICATIONS

Maruoka et al. "Methylaluminum Bis(4-bromo-2,6-di-tert-butylphenoxide) as a Key Reagent for Effecting Primary alpha-Alkylation of Carbonyl Compounds" Journal of the American Chemical Society, 114:4422-4423 (1992).
Oehlschlager et al. "Structure, Chirality, and Field Testing of a Male-Produced Aggregation Pheromone of Asian Palm Weevil Rhynchophorus bilineatus (Montr.) (Coleoptera: Curculionidae)" Journal of Chemical Ecology, 21 (10):1619-1629 (1995).
Perez et al. "Pheromone Chirality of Asian Palm Weevils, Rhynchophorus ferrugineus (OLIV.) and R. vulneratus (PANZ.) (Coleoptera: Curculionidae)" Journal of Chemical Ecology, 22(2):357-368 (1996).
Dang et al. "A facile synthesis of racemic aggregation pheromones of palm pests, Rhinoceros beetle and Rhynchophorous weevil" ARKIVOC, 2017(5):187-195 (2017).
Extended European Search Report corresponding to European Patent Application No. 19217002.5 (6 pages) (dated May 7, 2020).
Onaka et al. "A Convenient Method for the Direct Preparation of Ketones from 2-(6-(2-Methoxyethyl)Pyridyl) Carboxylates and Alkyl Iodides by Use of Zinc Dust and a Catalytic Amount of Nickel Dichloride" Chemistry Letters, pp. 531-534 (1981).
U.S. Appl. No. 16/722,123, filed Dec. 20, 2019, Miyake et al.
Ahn et al. "Cerium(III) Chloride Remarkably Increases the Rates of Formation and Yields of Ketones in the Reaction of Lithium Carboxylates with Organolithiums" Tetrahedron Letters, 35(2):203-208 (1994).
Jorgenson, Margaret J. "Preparation of Ketones from the Reaction of Organolithium Reagents with Carboxylic Acids" Organic Reactions, Chapter 1, pp. 1-97 (1970).
Rubottom et al. "Preparation of Methyl Ketones by the Sequential Treatment of Carboxylic Acids with Methyllithium and Chlorotrimethylsilane" Journal of Organic Chemistry, 48:1550-1552 (1983).

* cited by examiner

Primary Examiner — Rosalynd A Keys
(74) Attorney, Agent, or Firm — Myers Bigel, P.A.

(57) ABSTRACT

The present invention provides a process for preparing 4-methyl-5-nonanone of the following formula (3), the process comprising at least a step of subjecting pentanoic anhydride of the following formula (1) and a 2-pentyl nucleophilic reagent of the following general formula (2), in which M represents Li, $MgZ^1$, or $ZnZ^1$, wherein $Z^1$ represents a halogen atom or a 2-pentyl group, to a nucleophilic substitution reaction to produce 4-methyl-5-nonanone (3), as well as a process for preparing 4-methyl-5-nonanol of the following formula (7), the process comprising at least steps of preparing 4-methyl-5-nonanone and subjecting the obtained 4-methyl-5-nonanone and a reducing agent to a reduction reaction to produce 4-methyl-5-nonanol (7).

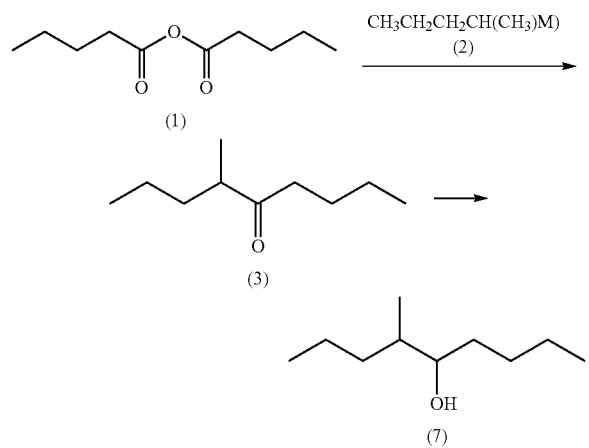

16 Claims, No Drawings

PROCESSES FOR PREPARING 4-METHYL-5-NONANONE AND 4-METHYL-5-NONANOL

CROSS-REFERENCE TO RELATED APPLICATION

This U.S. nonprovisional application claims priority to Japanese Application No. 2018-239546 filed Dec. 21, 2018, the entire contents of which are incorporated herein by reference.

TECHNICAL FIELD

The present invention relates to processes for preparing 4-methyl-5-nonanone and 4-methyl-5-nonanol which are known as an aggregation pheromone of red palm weevil (scientific name; *Rhynchophorus ferrugineus* e.g., *Rhynchophorus ferrugineus* Olivier) which is a pest of palm trees.

BACKGROUND ART

The red palm weevil is a key pest of plants of the family Palmae such as date palm, coconut, oil palm, and betel palm. Adults of the red palm weevil enter the trunk of a palm tree and lay eggs therein. Meanwhile, their larvae eat the inside of the tree, whereby weakening and eventually killing the plant. The red palm weevil is a species native in South Asia and Melanesia. It has spread to Southeast Asia, Middle East, North Africa, Europe, the United States of America, and others and is now causing a serious damage to palmae plants over wide areas. Adults and larvae of the red palm weevil move into a palm tree, so that they cannot easily be controlled by an insecticide. Mass trapping with an aggregation pheromone has been applied throughout the world to control the insect.

It has been revealed that the aggregation pheromone of the red palm weevil is a 10:1 to 9:1 (weight ratio) mixture of 4-methyl-5-nonanone and 4-methyl-5-nonanol (Non-Patent Literature 1, mentioned below). Processes for synthesizing these compounds were reported. 4-Methyl-5-nonanone is synthesized by activating 5-nonanone with methylaluminum bis(4-bromo-2,6-di-tert-butylphenoxide) at −40° C. in a solvent dichloromethane, which is then reacted with methyl triflate (Non-Patent Literature 2, mentioned below). 4-Methyl-5-nonanol is synthesized by reacting 2-methyl-1-pentanol with n-butyllithium (Non-Patent Literature 3, mentioned below).

LIST OF THE PRIOR ART

[Non-Patent Literature 1] A. C. Oehischlager et al., J. Chem. Ecol., 1996, 22(2), 357-368.

[Non-Patent Literature 2] H. Yamamoto et at, J. Am. Chem, Soc., 1992, 114, 4422-4423.

[Non-Patent Literature 3] A. C. Oehlschlager et al., J. Chem. Ecol., 1995, 21(10), 1619-1629.

SUMMARY OF THE INVENTION

However, in Non-Patent Literature 2, carcinogenic methyl triflate is used as a methylating agent and, further, a special aluminum reagent not easily available as a general reagent is used in an equivalent amount or more. Moreover, in Non-Patent Literature 2, a reactor equipped with a special cooling device is required for carrying out the reaction at −40° C., but such a reactor is difficult to industrially manufacture. In Non-Patent Literature 3, the expensive lithium reagent is used and, further, a yield is as low as 67%. This is presumable because an alcohol formed in the nucleophilic addition reaction between 2-methyl-1-pentanal and n-butyllithium changes to a corresponding ketone by hydride transfer, and the ketone reacts with n-butyllithium again to form a tertiary alcohol as a by-product.

The present invention has been made in these circumstances, and aims to provide efficient and economical processes for preparing 4-methyl-5-nonanone and 4-methyl-5-nonanol.

As a result of the intensive researches to overcome the aforesaid problems of the prior art, the present inventors have found that 4-methyl-5-nonanone is prepared in a high yield and a high purity by a nucleophilic substitution reaction between pentanoic anhydride which is synthesized in a large amount at low costs and a 2-pentyl nucleophilic reagent which is industrially available and is conveniently prepared, and thus have completed the present invention. The present inventors have also found that 4-methyl-5-nonanol is prepared in a high yield and a high purity by subjecting 4-methyl-5-nonanone to a reduction reaction, and thus have completed the present invention.

In one aspect of the present invention, there is provided a process for preparing 4-methyl-5-nonanone of the following formula (3);

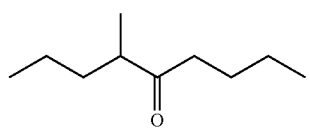

(3)

the process comprising at least a step of
subjecting pentanoic anhydride of the following formula (1):

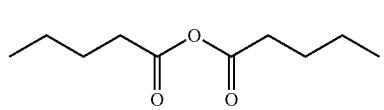

(1)

and a 2-pentyl nucleophilic reagent of the following general formula (2):

$$CH_3CH_2CH_2CH(CH_3)M \qquad (2)$$

in which M represents Li, $MgZ^1$, or $ZnZ^1$, wherein $Z^1$ represents a halogen atom or a 2-pentyl group,
to a nucleophilic substitution reaction to produce 4-methyl-5-nonanone (3).

In another aspect of the present invention, there is also provided a process for preparing 4-methyl-5-nonanol of the following formula (7):

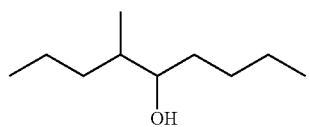

(7)

the process comprising at least steps of
preparing 4-methyl-5-nonanone according to the aforesaid process, and subjecting the obtained 4-methyl-5-nonanone and a reducing agent to a reduction reaction to produce 4-methyl-5-nonanol (7).

The present invention makes it possible to prepare 4-methyl-5-nonanone and 4-methyl-5-nonanol both in a high purity, a high yield, at low costs and in shorter steps.

DETAILED DESCRIPTION OF THE INVENTION

A. Process for Preparing 4-methyl-5-nonanone (3)

First, a process for preparing a 2-halopentane compound of the following general formula (5) to be used as a raw material for a 2-pentyl nucleophilic reagent to be used in a process for preparing 4-methyl-5-nonanone will be described hereinafter. The 2-halopentane compound (5) is obtained in a known synthesis process. The 2-halopentane compound (5) is obtained, for example, by halogenating a 2-pentanol of the following formula (4) by a halogenating agent, as shown in the following chemical reaction formula.

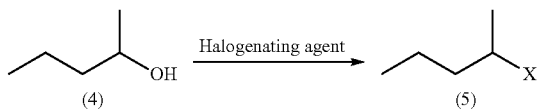

Examples of the 2-pentanol (4) include (R)-2-pentanol of the following formula (4-1), (S)-2-pentanol of the following formula (4-2), and a racemate and scalemic mixtures thereof.

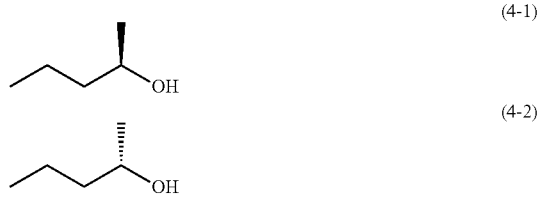

The 2-pentanol (4) may be commercially available one or may be synthesized in house.

Examples of the halogenating agent include sulfonyl halide compounds, thionyl halide compounds, sulfuryl halide compounds, hydrogen halide compounds, triarylhalophosphonium halide compounds, phosphorus trihalide compounds, and phosphorus pentahalide compounds. Examples of the halogenation with the halogenating agent include chlorination, bromination, and iodination.

The sulfonyl halide compound is represented by the following formula (6).

$XSO_2R$ (6)

X in the sulfonyl halide compound (6) represents a halogen atom. Examples of the halogen atom include a chlorine atom, a bromine atom, and an iodine atom.

R in the sulfonyl halide compound (6) represents a monovalent hydrocarbon group having from 1 to 7 carbon atoms, preferably from 1 to 3 carbon atoms.

Examples of the monovalent hydrocarbon group, R, include linear saturated hydrocarbon groups such as methyl, ethyl, n-propyl, n-butyl, n-pentyl, n-hexyl, and n-heptyl groups; branched saturated hydrocarbon groups such as isopropyl, 2-methylpropyl, and 2-methylbutyl groups; linear unsaturated hydrocarbon groups such as a 2-propenyl group; branched unsaturated hydrocarbon groups such as a 2-methyl-2-propenyl group; cyclic saturated hydrocarbon groups such as a cyclopropyl group; and aralkyl groups such as phenyl, o-tolyl, m-tolyl, and p-tolyl groups. Hydrocarbon groups in isomeric relation with the aforesaid ones are also included. A part of the hydrogen atoms of the hydrocarbon group may be substituted with a methyl or ethyl group.

Specific examples of the sulfonyl halide compound (6) include methanesulfonyl halide compounds such as methanesulfonyl chloride, methanesulfonyl bromide, and methanesulfonyl iodide; p-toluenesulfonyl halide compounds such as p-toluenesulfonyl chloride, p-toluenesulfonyl bromide, and p-toluenesulfonyl iodide, and benzenesulfonyl halide compounds such as benzenesulfonyl chloride, benzenesulfonyl bromide, and benzenesulfonyl iodide.

Examples of the thionyl halide compound include thionyl chloride, thionyl bromide, and thionyl iodide.

Examples of the sulfuryl halide compound include sulfuryl chloride, sulfuryl bromide, and sulfuryl iodide.

Examples of the hydrogen halide compound include hydrogen chloride, hydrogen bromide, and hydrogen iodide.

Examples of the triarylhalophosphonium halide compound include triphenylhalophosphonium halide compounds such triphenylchlorophosphonium chloride, triphenylbromophosphonium bromide, and triphenyliodophosphonium iodide; and tritolylhalophosphonium halide compounds such as tritolylchlorophosphonium chloride, tritolylbromophosphonium bromide, and tritolyliodophosphonium iodide.

The triarylhalophosphonium halide compound can be prepared by reacting a triarylphosphine compound, such as triphenylphosphine, with a chlorine molecule, a bromine molecule, an iodine molecule, carbon tetrachloride, or carbon tetrabromide.

Examples of the phosphorus trihalide compound include phosphorus trichloride, phosphorus tribromide, and phosphorus triiodide.

Examples of the phosphorus pentahalide compound include phosphorus pentachloride, phosphorus pentabromide, and phosphorus pentaiodide.

As the halogenating agent, the sulfonyl halide compound (6) and the triarylphosphonium halide compound are preferred in view of easy handling because they do not generate a by-product gas, with the sulfonyl halide compound (6) being more preferred.

An amount of the halogenating agent is preferably from 1.0 to 4.0 mol per mol of the 2-pentanol (4) in view of the reactivity.

The halogenation reaction may be carried out in the presence of a basic compound as described below, if necessary. Examples of the basic compound include trialkylamine compounds, dialkylamine compounds, monoalkylamine compounds, pyrrolidine compounds, piperidine compounds, pyridine compounds, pyrimidine compounds, aniline compounds, and imidazole compounds, and 3-pyrroline, and pyrrole.

Examples of the trialkylamine compounds include trimethylamine, triethylamine, tributylamine, and N,N-diisopropylethylamine.

Examples of the dialkylamine compounds include dimethylamine, diethylamine, and dibutylamine.

Examples of the monoalkylamine compound include ethylamine, propylamine, butylamine, hexylamine, and heptylamine.

Examples of the pyrrolidine compounds include pyrrolidine, N-methylpyrrolidine, methylpyrrolidine, N-ethylpyrrolidine, N-butylpyrrolidine, and 1-(2-aminoethyl)pyrrolidine.

Examples of the piperidine compounds include piperidine, N-methylpiperidine, N-ethylpiperidine, 4-aminomethyl-1-butylpiperidine, N-aminopiperidine, 2-methylpiperidine (pipecoline), and 2,6-dimethylpiperidine.

Examples of the pyridine compound include pyridine, 2-methylpyridine (α-picoline), 3-methylpyridine (β-picoline), 4-methylpyridine (γ-picoline), 2-ethylpyridine, 3-ethylpyridine, 4-ethylpyridine, 2,4,6-trimethylpyridine, 2,3,5-trimethylpyridine, 2,6-dimethylpyridine (2,6-lutidine), 2,3-dimethylpyridine (2,3-lutidine), 2,4-dimethylpyridine (2,4-lutidine), 2,5-dimethylpyridine (2,5-lutidine), 3,4-dimethylpyridine (3,4-lutidine), 3,5-dimethylpyridine (3,5-lutidine), 2-cyanopyridine, 3-cyanopyridine, 4-cyanopyridine, 4-diethylaminopyridine, 4-piperidinopyridine, 2-aminomethylpyridine, and 3-aminomethylpyridine.

Examples of the pyrimidine compounds include pyrimidine and 2-methylpyrimidine.

Examples of the aniline compounds include aniline, N,N-dimethylaniline, N,N-diethylaniline, N,N-diisopropylaniline, N-methylaniline, N-ethylaniline, and N-isopropylaniline.

Examples of the imidazole compounds include imidazole and 2-methylimidazole.

Preferred basic compounds are the pyridine compound such as pyridine, and the aniline compound such as N,N-diethylaniline.

An amount of the basic compound is preferably from 0.0 to 3.5 mol, more preferably from 1.0 to 3.0 mol, per mol of the 2-pentanol (4).

A solvent may be used in the halogenation reaction, if necessary. Examples of the solvent include hydrocarbon solvents such as toluene, pentane, hexane, heptane, cyclohexane, and cyclohexene; ether solvents such as tetrahydrofuran, 4-methyltetrahydropyran, and diethyl ether; and polar solvents such as N,N-dimethylformamide, N,N-dimethylacetamide, acetonitrile, and 1-methyl-2-pyrrolidone.

The solvent may be used either alone or in combination thereof. The solvent may be commercially available one.

An optimum solvent differs in view of the reactivity, depending on a halogenating agent selected. For example, the polar solvent is preferred when the sulfonyl halide compound is used as the halogenating agent, and the ether solvent and/or the polar solvent is preferred when the triarylhalophosphonium halide compound is used.

An amount of the solvent is preferably from 0 to 1000 g per mol of the 2-pentanol (4) in view of the reactivity.

A metal halide may be used in the halogenation reaction, if necessary to enhance a concentration of halide ions to thereby improve the reactivity. Examples of the metal halide include lithium halides such as lithium chloride, lithium bromide, and lithium iodide; and sodium halides such as sodium chloride, sodium bromide, and sodium iodide.

The metal halide may be used either alone or in combination thereof. The metal halide may be commercially available one.

A temperature in the halogenation reaction differs, depending on a halogenating agent used and is preferably from −20 to 189° C. in view of the reactivity. When the sulfonyl halide compound is used as the halogenating agent, the temperature is preferably from −10 to 80° C. When the halogen molecule is used as the halogenating agent, the temperature is preferably from −10 to 40° C.

A reaction time differs, depending on a halogenating agent used and/or a production scale and is preferably from 4 to 35 hours in view of the reactivity.

X in the 2-halopentane compound (5) represents a halogen atom. Examples of the halogen atom include a chlorine atom, a bromine atom, and an iodine atom.

Examples of the 2-halopentane compound (5) include (R)-2-halopentane compounds of the following formula (5-1) and (S)-2-halopentane compounds of the following formula (5-2), and a racemate and scalemic mixtures thereof.

(5-1)

(5-2)

Examples of the (R)-2-halopentane compounds (5-1) include (R)-2-chloropentane, (R)-2-bromopentane, and (R)-2-iodopentane.

Examples of the (S)-2-halopentane compounds (5-2) include (S)-2-chloropentane, (S)-2-bromopentane, and (S)-2-iodopentane.

The 2-halopentane compound (5) may be commercially available one or may be synthesized in house.

In a case where a thionyl halide compound which is a typical halogenating agent is used in the halogenation reaction of the 2-pentanol (4), a lame amount of 1-pentene and/or 2-pentene may sometimes be by-produced due to simultaneous progress of an elimination reaction, while a 2-halopentane compound (5) is formed.

In the halogenation reaction of the 2-pentanol (4) with a sulfonyl halide compound, it is sometimes necessary to use a metal halide in combination to increase the reaction efficiency because an intermediate, sulfonate compound, in the halogenation reaction may sometimes remain unreacted.

The present inventors however have found that the 2-halopentane compound (5) is prepared efficiently by carrying out the halogenation reaction in the presence of the basic compound and using the sulfonyl halide compound (6) as the halogenating agent to thereby suppress the elimination reaction.

Thus, the halogenation reaction is carried out without a costly metal halide, which is industrially advantageous.

In addition, by-production of a 1-halopentane compound caused by the addition of a hydrogen halide to 1-pentene and/or 2-pentene is suppressed, so that the 2-halopentane compound (5) can be prepared in an improved purity.

When the sulfonyl halide compound (6) is used as the halogenating agent and the halogenation reaction is carried out in the presence of the basic compound, a molar ratio of the basic compound to the sulfonyl halide compound (6) is preferably from 1.00 to 2.00, more preferably from 1.10 to 1.50, in view of the reactivity.

Next, will be explained a step of the following chemical reaction for preparing a 2-pentyl nucleophilic reagent of the following general formula (2) from the aforesaid 2-halopentane compound (5).

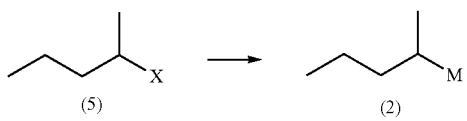

(5) → (2)

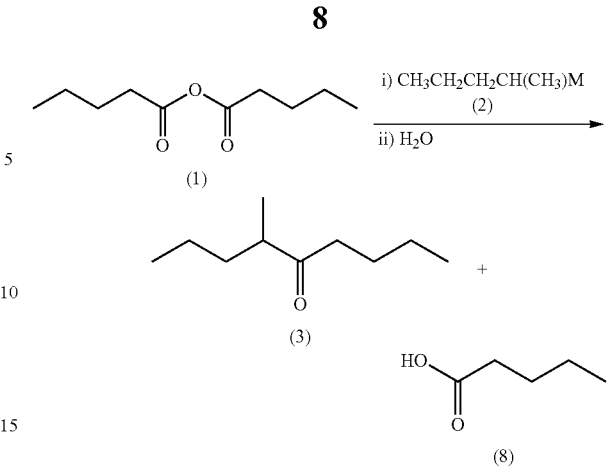

M in the 2-pentyl nucleophilic reagent (2) represents Li, $MgZ^1$, or $ZnZ^1$, and $Z^1$ represents a halogen atom or a 2-pentyl group. Examples of the halogen atom include a chlorine atom, a bromine atom, and an iodine atom.

Specific examples of the 2-pentyl nucleophilic reagent (2) include 2-pentylmagnesium halide reagents such as 2-pentyllithium, 2-pentylmagnesium chloride, and 2-pentylmagnesium bromide; and 2-pentylzine reagents such as bis-(2-pentyl)zinc. The 2-pentylmagnesium halide reagents are preferred in view of the versatility.

The 2-pentyl nucleophilic reagent (2) may be used either alone or in combination thereof. The 2-pentyl nucleophilic reagent (2) may be commercially available one or may be synthesized in house.

The aforesaid step can be carried out in a manner known per se in the art. For instance, the 2-halopentane compound is reacted with magnesium in a solvent to produce the 2-pentylmagnesium halide reagent, as shown in the following chemical reaction formula.

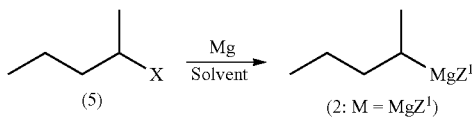

(5) → (2: M = MgZ¹)

The 2-halopentane compound (5) may be used either alone or in combination thereof.

An amount of magnesium to be used in preparing the 2-pentylmagnesium halide reagent from the 2-halopentane compound (5) is preferably from 1.0 to 2.0 gram atoms per mol of the 2-halopentane compound (5) in view of the completion of the reaction.

Examples of the solvent used in preparing the 2-pentylmagnesium halide reagent from the 2-halopentane compound (5) include ether solvents such as tetrahydrofuran, diethyl ether, and 4-methyltetrahydropyran; and hydrocarbon solvents such as toluene, xylene, and hexane. Tetrahydrofuran is preferred in view of the reaction rate in the formation of the Grignard reagent.

An amount of the solvent is preferably from 100 to 1000 g per mol of the 2-halopentane compound (5) in view of the reactivity.

A reaction temperature differs, depending on a solvent used and is preferably from 30 to 120° C. in view of the reactivity.

A reaction time differs, depending on a solvent used and/or a production scale and is preferably from 1 to 30 hours in view of the reactivity.

Next, a process of the following chemical reaction for preparing the 4-methyl-5-nonanone (3) will be explained. This preparation process includes a nucleophilic substitution reaction between pentanoic anhydride of the following formula (1) and the aforesaid 2-pentyl nucleophilic reagent (2), and a subsequent hydrolysis to obtain the 4-methyl-5-nonanone (3).

The pentanole anhydride (1) may be commercially available one or may be prepared in house by a condensation reaction of pentanoic acid (8).

The 2-pentyl nucleophilic reagent (2) is as described above. The 2-pentyl nucleophilic reagent (2) may be used either alone or in combination thereof. The 2-pentyl nucleophilic reagent (2) may be commercially available one or may be synthesized in house.

A solvent may be used in the aforesaid nucleophilic substitution reaction, if necessary. Examples of the solvent include hydrocarbon solvents such as toluene, xylene, and hexane; ether solvents such as tetrahydrofuran, 4-methyltetrahydropyran, and diethyl ether; and polar solvents such as N,N-dimethylformamide, N,N-dimethylacetamide, N-methylpyrrolidone, dimethyl sulfoxide, and acetonitrile. Toluene, tetrahydrofuran, 4-methyltetrahydropyran, and acetonitrile are preferred, with tetrahydrofuran being more preferred, in view of the reactivity.

The solvent may be used either alone or in combination thereof. The solvent may be commercially available one.

An amount of the solvent is preferably from 30 to 2000 g per mol of the pentanoic anhydride (1) in view of the reactivity.

A temperature of the nucleophilic substitution reaction differs, depending on the 2-pentyl nucleophilic reagent (2) used and is preferably from −78 to 70° C., more preferably from −20 to 25° C., in view of the reactivity.

A reaction time differs, depending on a solvent used and/or a production scale and is preferably from 3 to 45 hours in view of the re-activity.

The aforesaid hydrolysis is carried out using an acid and water.

Examples of the acid include organic acids such as formic acid, acetic acid, trifluoroacetic acid, dichloroacetic acid, oxalic acid, tartaric acid, citric acid, p-toluenesulfonic acid, benzenesulfonic acid, and methanesulfonic acid; and inorganic acids such as hydrochloric acid, hydrobromic acid, hydroiodic acid, sulfuric acid, nitric acid, phosphoric acid, and boric acid. Formic acid, acetic acid, and hydrochloric acid are preferred in view of the economy.

An amount of the acid is preferably from 1 to 5 mol per mol of the pentanoic anhydride (1) in view of the reactivity.

An amount of water is preferably from 100 to 1000 g per mol of the pentanoic anhydride (1) in view of the solubility.

Examples of the 4-methyl-5-nonanone (3) include (4R)-4-methyl-5-nonanone of the following formula (3-1) and (4S)-4-methyl-5-nonanone of the following formula (3-2), and a racemate and scalemic mixtures thereof.

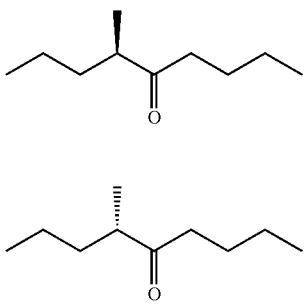

(3-1)

(3-2)

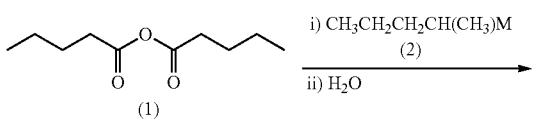

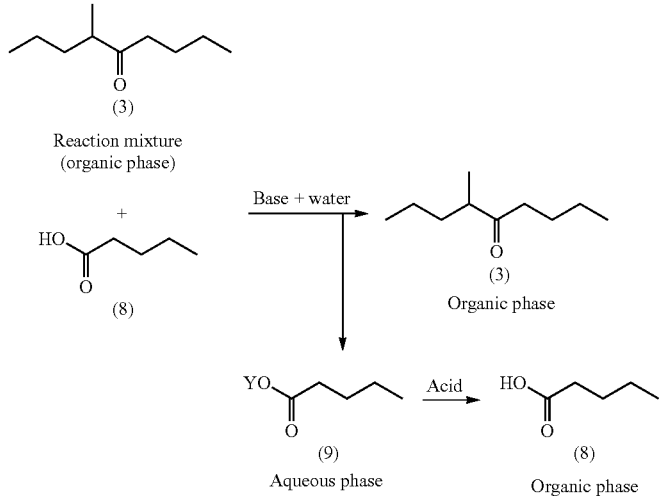

During or after the aforesaid nucleophilic substitution reaction, pentanoic acid which was by-produced in the nucleophilic substitution reaction may be recovered; the recovered pentanoic acid is condensation-reacted into pentanoic anhydride (1); and the pentanoic anhydride (1) thus obtained is used in the nucleophilic substitution reaction or is used in a subsequent nucleophilic substitution reaction as a raw material for the subsequent nucleophilic substitution reaction to repeat the subsequent nucleophilic substitution reaction.

First, the step of recovering pentanoic acid which was by-produced in the nucleophilic substitution reaction will be explained.

In the nucleophilic substitution reaction where the 4-methyl-5-nonanone (3) is produced, pentanoic acid (8) is by-produced from the pentanoic anhydride (1).

Examples of a method for recovering the pentanoic acid (8) include a method of separating the pentanoic acid (8) from the 4-methyl-5-nonanone (3) and recovering the pentanoic acid (8) in post-treatment after the nucleophilic substitution reaction, a method of separating the pentanoic acid (8) from the 4-methyl-5-nonanone (3) by silica gel column chromatography and recovering the pentanoic acid (8), and a method of separating the pentanoic acid (8) from the 4-methyl-5-nonanone (3) by distillation and recovering the pentanoic acid (8). For example, the method of separating the pentanoic acid (8) from the 4-methyl-5-nonanone (3) and recovering the pentanoic acid (8) in the post-treatment after the nucleophilic substitution reaction is preferred, because the separation of the pentanoic acid (8) from the 4-methyl-5-nonanone (3) is easy.

The aforesaid recovering method in the post-treatment is specifically shown by the following chemical reaction formula. As described above, the reaction mixture (organic phase) containing the 4-methyl-5-nonanone (3) and the pentanoic acid (8) obtained in the nucleophilic substitution reaction is neutralized by adding water and a base thereto successively or simultaneously or neutralized in the presence of an aqueous solution of a base to obtain an organic phase containing the 4-methyl-5-nonanone (3) and an aqueous phase containing a salt of pentanoic acid (9) (neutralization step). After separation of the aqueous phase, an acid is added thereto to liberate the pentanoic acid (8). Thus, the pentanoic acid (8) is obtained (liberation step).

The pentanoic acid (8) is neutralized with the base into the salt of pentanoic acid (9) in the neutralization step. The salt of pentanoic acid (9) is soluble in water. Therefore, the 4-methyl-5-nonanone (3) is easily separated from the salt of pentanoic acid (9). By liquid separation, the organic phase containing the 4-methyl-5-nonanone (3) and the aqueous phase containing the salt of pentanoic acid (9) is obtained.

Examples of the base include alkali metal hydroxides such as lithium hydroxide, sodium hydroxide, and potassium hydroxide; alkaline earth metal hydroxides such as calcium hydroxide, magnesium hydroxide, and barium hydroxide; alkali metal carbonates such as sodium carbonate and potassium carbonate; alkaline earth metal carbonates such as calcium carbonate, magnesium carbonate, and barium carbonate; alkali metal hydrogen carbonates such as sodium hydrogen carbonate and potassium hydrogen carbonate; and alkaline earth metal hydrogen carbonates such as calcium hydrogen carbonate and magnesium hydrogen carbonate. The alkali metal hydroxides such as sodium hydroxide are preferred in view of handling.

An amount of the base is preferably from 1.0 to 5.0 mol per mol of the pentanoic anhydride (1) used in the aforesaid nucleophilic substitution reaction in view of a recovery yield.

The base may be used either alone or in combination thereof. The base may be commercially available one.

When the base is in a solid form, it may be used as such or may be dissolved in a solvent and/or water used in the nucleophilic substitution reaction.

An amount of water is preferably from 300 to 3000 g per mol of the pentanoic anhydride (1) used in the aforesaid nucleophilic substitution reaction in view of the solubility of the salt of pentanoic acid (9).

A temperature of the neutralization reaction is preferably from −20 to 70° C., more preferably from 0 to 40° C., in view of the reactivity.

A reaction time differs, depending on a production scale and/or heat removal ability and is preferably from 0.1 to 20 hours in view of the reactivity.

A pH of the aqueous phase in the neutralization step is preferably 10.0 or higher, more preferably from 12.0 to 14.0, in view of the recovery yield of the pentanoic acid (8). The pH may be determined by, for example, a pH test strip or a pH meter after adjusting a temperature of the liquid object at 2.5° C.

The salt of pentanoic acid is represented by the following formula (9) wherein Y represents Li, Na, K, $CaZ^2$, $MgZ^2$, or $BaZ^2$, and $Z^2$ represents a carboxylate ion of pentanoic acid, OH, or $HCO_3$.

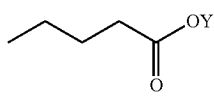

(9)

Preferred examples of the salt of pentanoic acid (9) depend on a base used, and generally include alkali metal salts of pentanoic acid such as sodium pentanoate and potassium pentanoate; and alkaline earth metal salts of pentanoic acid such as calcium pentanoate, magnesium pentanoate, and barium pentanoate.

Next in the liberation step, an acid is added to the aqueous phase containing the salt of pentanoic acid (9) to make the phase acidic so as to have the pentanoic acid (8) liberated; and the liberated pentanoic acid (8) is recovered by separating the pentanoic acid (8) from the aqueous phase.

Examples of the acid to be used in the liberation step include organic acids such as formic acid, acetic acid, trifluoroacetic acid, dichloroacetic acid, oxalic acid, tartaric acid, citric acid, p-toluenesulfonic acid, benzenesulfonic acid, and methanesulfonic acid; and inorganic acids such as hydrochloric acid, hydrobromic acid, hydroiodic acid, sulfuric acid, nitric acid, phosphoric acid, and boric acid. Hydrochloric acid is preferred in view of the economy.

The acid may be used either alone or in combination thereof. The acid may be commercially available one.

When the acid is in a solid form, it may be used as such or dissolved in the solvent and/or water used in the nucleophilic substitution reaction.

An amount of the acid is preferably from 1.0 to 6.0 mol per mol of the pentanoic anhydride (1) used in the aforesaid nucleopbilic substitution reaction in view of the recovery yield.

A temperature of the liberation reaction is preferably from −20 to 70° C., more preferably from 0 to 40° C., in view of the reactivity.

A reaction time differs, depending on a production scale and/or heat removal ability and is preferably from 0.5 to 20 hours in view of the reactivity.

A pH of the aqueous phase is preferably 1.0 or lower, more preferably from −1.0 to +1.0, in view of the recovery yield of the pentanoic acid (8). The pH may be determined, few example, by a pH test strip or a pH meter after adjusting the temperature of the liquid object at 25° C.

In the liberation step, a solvent may be added, such as a hydrocarbon solvent such as toluene, xylene, pentane, hexane, or heptane; an ether solvent such as tetrahydrofinan, 4-methyltetrahydropyran, or diethyl ether; or a polar solvent such as methyl acetate, ethyl acetate, or acetonitrile. However, the solvent should be removed later, so that the reaction is conducted preferably without a solvent, The pentanoic acid (8) thus recovered is converted into pentanoic anhydride by a condensation reaction and can be repeatedly used as a raw material for the nucleophilic substitution reaction, which is economically advantageous.

Next, will be explained a step of the following chemical reaction formula for subjecting commercial or recovered pentanoic acid (8) to a condensation reaction to obtain the pentanoic anhydride (1).

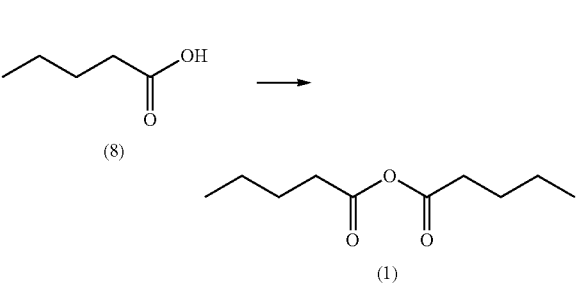

The condensation reaction may proceed under heating. A condensing agent is preferably used in view of the reaction efficiency.

Examples of the condensing agent include acid anhydrides of a carboxylic acid compound having from 1 to 4 carbon atoms such as formic anhydride, acetic anhydride, propionic anhydride, butanoic anhydride, and 2-methylpropanoic anhydride; carboxylic acid compounds such as formic acid, acetic acid, trifluoroacetic acid, dichloroticetic acid, oxalic acid, tartaric acid, and citric acid; sulfonic acid compounds such as p-toluenesulfonic acid, benzenesulfonic acid, and methanesulfonic acid; inorganic acids such as hydrochloric acid, hydrobromic acid, hydroiodic acid, sulfuric acid, nitric acid, phosphoric acid, and boric acid; and carbodiimide compounds such as N,N'-dicyclobexylcarbodiimide (DCC), 1-(3-dimethylaminopropyl)-3-ethylcarbodiimide (EDC), and N,N'-diisopropylcarbodiimide (DIC). Formic acid, acetic acid, and acetic anhydride are preferred, with acetic anhydride being more preferred, in view of the handling.

The condensing agent may be used either alone or in combination thereof. The condensing agent may be commercially available one.

An amount of the condensing agent is preferably from 1.0 to 4.0 mol, more preferably from 1.3 to 2.7 mol, per mol of the pentanoic acid (8) in view of the reactivity.

In the condensation reaction, a solvent may be used, if necessary. Examples of the solvent include hydrocarbon solvents such as toluene, xylene, and hexane; ether solvents such as tetrahydrofuran and diethyl ether; and polar solvents such as N,N-dimethylformamide N,N-dimethylacetamide, N-methylpyrrolidone, dimethyl sulfoxide, and acetonitrile.

The solvent may be used either alone or in combination thereof. The solvent may be commercially available one.

An amount of the solvent is preferably from 0 to 2000 g per mol of the pentanoic acid (8) in view of the reactivity.

When the condensing agent used is in a liquid form, the condensing agent may work also as a solvent. Examples of the liquid condensing agent include acid anhydrides of carboxylic acids having from 1 to 4 carbon atoms such as formic anhydride, acetic anhydride, propionic anhydride, butanoic anhydride, and 2-methylpropanoic anhydride; and carboxylic acids such as formic acid, acetic acid, trifluoroacetic acid, dichloroacetic acid, oxalic acid, tartaric acid, and citric acid. By using them, use of another solvent is not required or an amount thereof can be reduced.

An amount of the condensing agent which works also as a solvent is preferably more than 4.0 and 10.0 mol or less, more preferably from 4.5 to 8.5 mol, per mol of the pentanoic acid (8) in view of the productivity.

A temperature of the condensation reaction differs, depending on a solvent used and/or a degree of evacuation and is preferably from 35 to 189° C. in view of the reactivity.

A reaction time differs, depending on a solvent used and/or a production scale and is preferably from 4 to 35 hours in view of the reactivity.

The condensation reaction may be carried out while distilling off water generated by dehydration condensation and/or a carboxylic acid generated when an acid anhydride is used as the condensing agent, an acid anhydride generated by a disproportionation reaction, and other by-products under heating and/or reduced pressure to enhance the condensation reaction.

Conditions of the distillation differ, depending on reaction conditions and/or a condensing agent used. For example, when acetic anhydride is used as the condensing agent (including a case Where acetic anhydride works also as a solvent), the pentanoic acid (8) is reacted with acetic anhydride at normal pressure (760 mmHg) at a temperature (internal temperature) of the reaction mixture in a reactor of from 140 to 180° C. for 0.5 to 10 hours to form acetic pentanoic anhydride and acetic acid. Next, the formation of acetic pentanoic anhydride is continued at 140 to 180° C. and normal pressure while distilling acetic acid off until an acetic content becomes preferably at most 10.0%, more preferably 0.1 to 5.0%, in the distillate containing at least acetic acid, acetic anhydride, and acetic pentanoic anhydride.

A content of acetic acid in the distillate containing at least acetic acid, acetic anhydride, and acetic pentanoic anhydride is defined by the following equation.

Content of acetic acid in the distillate containing at least acetic acid, acetic anhydride, and acetic pentanoic anhydride={(peak area of acetic acid)/(sum of peak areas of acetic acid, acetic anhydride, and acetic pentanoic anhydride)}×100

The peak areas are determined by various analysis methods such as gas chromatography and liquid chromatography.

A disproportionation reaction of acetic pentanoic anhydride is caused at a pressure gradually reduced to from 55 to 75 mmHg and an internal temperature of from 140 to 180° C. to sufficiently form pentanoic anhydride and acetic anhydride. It is to be noted that the terra "internal temperature" means a temperature of the reaction mixture in the reactor and has the same meaning as a reaction temperature.

The acetic anhydride used as a condensing agent and the acetic anhydride formed by the disproportionation reaction are distilled off until the content of acetic anhydride in the distillate containing at least acetic anhydride, pentanol, acetic pentanoic anhydride, and pentanoic anhydride reaches preferably 1.0% or less, more preferably from 0.1 to 0.5%.

A content of acetic anhydride in the distillate containing at least acetic anhydride, pentanol, acetic pentanoic anhydride, and, pentanoic anhydride is defined by the following equation.

Content of acetic anhydride in the distillate containing at least acetic anhydride, pentanol, acetic pentane anhydride, and pentanoic anhydride={(peak area of acetic anhydride)/(sum of peak areas of acetic anhydride, pentanol, acetic pentanoic anhydride, and pentanoic anhydride)}×100

The peak areas are determined by various analysis methods such as gas chromatography and liquid chromatography.

Lastly, the pressure is reduced to from 1 to 10 mmHg and adjusting the internal temperature to from 90 to 150° C. to obtain pentanoic anhydride (1) efficiently.

B. Preparation of 4-methyl-5-nonanol (7)

A process for preparing 4-methyl-5-nonanol (7) in the following chemical reaction formula will be explained. This preparation process includes a step of forming 4-methyl-5-nonanol (7) by a reduction reaction between the 4-methyl-5-nonanone (3) prepared in the aforesaid step A and a reducing agent.

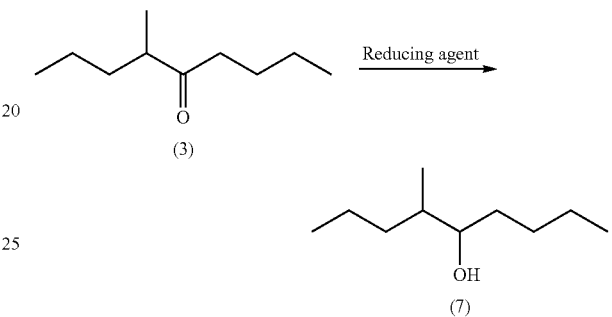

Examples of the reducing agent include alkali metal borohydrides such as lithium borohydride, sodium borohydride, and potassium borohydride; alkaline earth metal borohydrides such as magnesium borohydride and calcium borohydride; alkali metal cyanoborohydrides such as lithium cyanoborohydride, sodium cyanoborohydride, and potassium cyanoborohydride; alkaline earth metal cyanoborohydrides such as magnesium cyanoborohydride and calcium cyanoborohydride; alkali metal tri-sec-butyl borohydrides such as sodium tri-sec-butyl borohydride and lithium tri-see-butyl borohydride; and diisobutylaluminum hydride, sodium bis(2-methoxyethoxy)aluminum hydride, and lithium aluminum hydride. The alkali metal borohydrides such as sodium borohydride are preferred in view of the economy.

The reducing agent may be used either alone or in combination thereof. The reducing agent may be commercially available one.

An amount of the reducing agent differs, depending on the reducing agent used and is preferably from 0.25 to 5.0 mol per mol of the 4-methyl-5-nonanone (3) in view of the reactivity.

A solvent may be used in the reduction reaction, if necessary. Examples of the solvent include hydrocarbon solvents such as toluene, xylene, and hexane; ether solvents such as tetrahydrofuran, 4-methyltetrahydropyran anti diethyl ether; polar solvents such as N,N-dimethylformamide, N,N-dimethylacetamide, N-methylpyrrolidone, acetonitrile, dichloromethane, and chloroform; alcohol solvents such as methanol and ethanol; and water. A proper solvent may be selected, depending on a reducing agent used. For example, an alcohol solvent such as ethanol or a mixed solvent of the alcohol solvent with another solvent is preferred when the alkali metal borohydride is used as the reducing agent.

For example, a mixing ratio in weight in the mixed solvent of the alcohol solvent with water is preferably from 40.0:60.0 to 60.0:40.0 in view of the reactivity.

An amount of the solvent is preferably from 40 to 1000 g per mol of the 4-methyl-5-nonanone (3) in view of the reactivity.

The solvent may be used either alone or in combination thereof. The solvent may be commercially available one.

A base may be used in the reduction reaction, if necessary. Examples of the base include alkali metal hydroxides such as lithium hydroxide, sodium hydroxide, and potassium hydroxide; alkaline earth metal hydroxides such as calcium hydroxide, magnesium hydroxide, and barium hydroxide; alkali metal carbonates such as sodium carbonate and potassium carbonate; alkaline earth metal carbonates such as calcium carbonate, magnesium carbonate, and barium carbonate; alkali metal hydrogen carbonates such as sodium hydrogen carbonate and potassium hydrogen carbonate; and alkaline earth metal hydrogen carbonates such as calcium hydrogen carbonate and magnesium hydrogen carbonate. The alkali metal hydroxides such as sodium hydroxide are preferred in view of the handling.

The base may be used either alone or in combination thereof. The base may be commercially available one.

When the base is in a solid form, it may be added as such to the reaction mixture or may be dissolved in advance in a solvent to be used in the reduction reaction.

An amount of the base is preferably from 0.00 to 10.00 mol, more preferably from 0.01 to 8.00 mol, per mol of the 4-methyl-5-nonanone (3) in view of the reactivity.

A temperature of the reduction reaction is preferably from 0 to 100° C., more preferably from 10 to 60° C., in view of the reactivity.

A reaction, time differs, depending on a solvent used and/or a production scale and is preferably from 2 to 35 hours in view of the reactivity.

Examples of the 4-methyl-5-nonanol (7) include (4R,5R)-4-methyl-5-nonanol of the following formula (7-1), (4S,5S)-4-methyl-5-nonanol of the following formula (7-2), (4R, 5S)-4-methyl-5-nonanol of the following formula (7-3), and (4S,5R)-4-methyl-5-nonanol of the following formula (7-4), and a racemate, diastereomeric mixtures, and scalemic mixtures thereof.

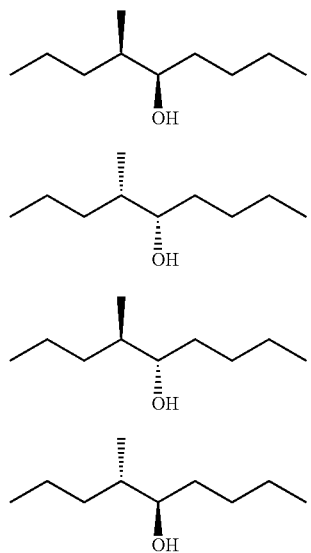

(7-1)

(7-2)

(7-3)

(7-4)

The compounds of the aforesaid formulas (7-1) and (7-2), and the compounds of the aforesaid formulas (7-3) and (7-4) may hereinafter he called "syn-form" and "anti-form", respectively.

The syn-form can be prepared selectively using an alkali metal tri-sec-butyl borohydride, and the anti-form can be prepared selectively using lithium aluminum hydride.

EXAMPLES

The present invention will be further described with reference to the following Examples. It should be construed that the invention is not limited to or by the Examples.

The term "purity" as used herein means an area percentage obtained by gas chromatography (GC) analysis, unless otherwise described. The term "production ratio" means a relative ratio in area percentages determined by GC analysis. The "yield" is calculated from area percentages obtained by GC analysis.

In each of Examples, monitoring of the reactions and calculation of the yield were carried out under the following GC conditions I.

<GC conditions I>: GC: Capillary gas chromatograph GC-2014, ex Shimadzu Corporation; column: DB-5, 0.25 mm×0.25 mmϕ×30 m; carrier gas: He (1.55 mL/min), detector: FID; column temperature: 70° C., elevated by 5° C./min, to 230° C.

A syn-form: anti-form ratio of the 4-methyl-5-nonanol (5) was analyzed under the following; GC conditions II.

<GC conditions>: GC: Capillary gas chromatograph GC-2014, ex Shimadzu Corporation; column: CYCLO-DEX-B, 0.25 mm×0:25 mmϕ×30 m; carrier gas: He (1.55 mL/min), detector: FID; column temperature: 70° C., elevated by 5° C./min, to 230° C.

The yield was calculated by the following equation in consideration of purities (% GC) of a raw material and a product.

Yield (%){[(weight of a product obtained by reaction×% GC)/molecular weight of a product]÷ [(weight of a starting material in reaction×% GC)/molecular weight of a starting material]}× 100

Example 1

Preparation of 2-chloropentane (5: X═Cl)

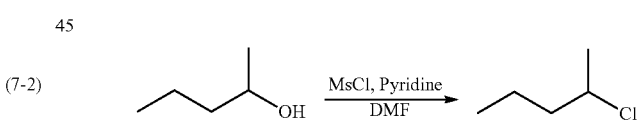

2-Pentanol (4) (296.71 g, 3.366 mol), pyridine (479.25 g, 6.06 mol), and N,N-dimethylformamide (DMF) (1009.80 g) were added to a reactor at room temperature and stirred at from 0 to 5° C. for 18 minutes. Next, methanesulfonyl chloride (MsCl) (6: X═Cl, R═Me) (539.81 g, 4.71 mol) was added dropwise to the reactor at an internal temperature of 10° C. or below. After the completion of the dropwise addition, the reaction mixture was heated to an internal temperature of from 60 to 65° C. and stirred for 11.5 hours. After lowering the internal temperature to 30° C., acetic acid (363.83 g) and water (1683.00 g) were added to the reaction mixture to cause phase separation and the aqueous phase thus obtained was removed. Then, sodium hydrogen carbonate (84.15 g) and water (841.50 g) were added to the organic phase to wash the same, followed by phase separation and removal of the aqueous phase. The organic phase thus obtained was concentrated at a reduced pressure and the residue was subjected to distillation at a reduced pressure to obtain 2-chloropentane (5: X=Cl) (300.80 g, 2.82 mol) in a yield of 83.8%. 1-Chloropentane and 1-pentene, i.e., regioisomers of 2-chloropentane (5: X=Cl), was not observed in GC analysis.

The following is the spectrum data of the 2-chloropentane (5: X=Cl) thus prepared.

[Nuclear magnetic resonance spectrum] $^1$H-NMR (500 MHz, CDCl$_3$): δ=0.92 (3H, t, J=7.3 Hz), 1.36-1.58 (2H, m), 1.50 (3H, d, J=4.6 Hz), 1.62-1.76 (2H, m), 4.04 (1H, td, J=1.5, 6.5 Hz); $^{13}$C-NMR (500 MHz, CDCl$_3$): δ=13.50, 19.85, 25.33, 42.41, 58.56 [Mass spectrum] EI-Mass spectrum (70 eV); m/z 105 (M$^+$−1), 91, 70, 55, 43, 27 [Infrared absorption spectrum](NaCl): ν=2962, 2933, 2875, 1458, 1380, 1270, 746, 672, 614

Example 2

Preparation of 2-chloropentane (5: X=Cl)

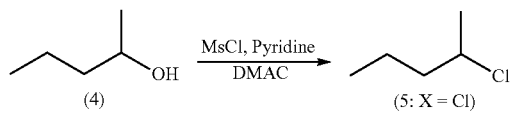

2-Pentanol (4) (296.71 g, 3.366 mol), pyridine (479.25 g, 6.06 mol), and N,N-dimethylacetamide (DMAC) (1009.80 g) were added to a reactor at room temperature and stirred at from 0 to 5° C. for 14 minutes. Next, methanesulfonyl chloride (MsCl) (6: X=Cl, R=Me) (539.81 g, 4.71 mol) was added dropwise to the reactor at an internal temperature of 10° C. or below. After the completion of the dropwise addition, the reaction mixture was heated to an internal temperature of from 60 to 65° C. and stirred for 9.5 hours. After lowering the internal temperature to 30° C., acetic acid (363.83 g) and water (1683.00 g) were added to the reaction mixture to cause phase separation and the aqueous phase thus obtained was removed. Then, sodium hydrogen carbonate (84.15 g) and water (841.50 g) were added to the organic phase to wash the same, followed by phase separation and removal of the aqueous phase. The organic phase thus obtained was concentrated at a reduced pressure and the residue was subjected to distillation at a reduced pressure to obtain 2-chloropentane (5: X=Cl) (289.39 g, 2.72 mol) in a yield of 80.7%. 1-Chloropentane and 1-pentene, i.e., regioisomers of 2-chloropentane (5: X=Cl), was not observed in GC analysis. The spectrum data of the 2-chloropentane (5: X=Cl) obtained above were the same as those of the 2-chloropentane (5: X=Cl) obtained in Example 1.

Example 3

Preparation of 2-chloropentane (5: X=Cl)

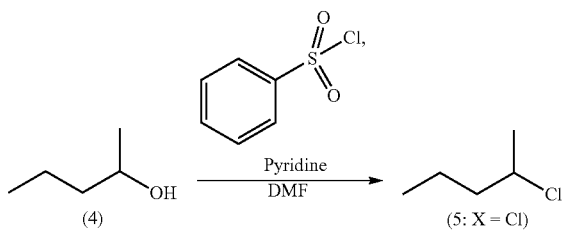

2-Pentanol (4) (88.15 g, 1.00 mol), pyridine (142.38 g, 1.80 mol), and N,N-dimethylformamide (DMF) (300.00 g) were added to a reactor at room temperature and stirred at from 0 to 5° C. for 39 minutes. Next, benzenesulfonyl chloride (6: X=Cl, R=Ph) (247.25 g, 1.40 mol) was added dropwise to the reactor at an internal temperature of 10° C. or below. After the completion of the dropwise addition, the reaction mixture was heated to an internal temperature of from 60 to 65° C. and stirred for 8 hours. After lowering the internal temperature to 30° C., acetic acid (108.09 g) and water (500.00 g) were added to cause phase separation and the aqueous phase thus obtained was removed. Then, sodium hydrogen carbonate (25.00 g) and water (500.00 g) were added to the organic phase to wash the same, followed by phase separation and removal of the aqueous phase. The organic phase thus obtained was concentrated in a reduced pressure and the residue was subjected to distillation in a reduced pressure to obtain 2-chloropentane (5: X=Cl) (80.97 g, 0.76 mol) in a yield of 76.0%. 1-Chloropentane and 1-pentene, i.e., regioisomers of 2-chloropentane (5: X=Cl), was not observed in GC analysis. The spectrum data of the 2-chloropentane (5: X=Cl) obtained above were the same as those of the 2-chloropentane (5: X=Cl) obtained in Example 1.

Example 4

Preparation of 2-chloropentane (5: X=Cl)

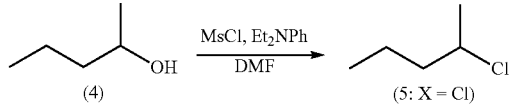

2-Pentanol (4) (88.15 g, 1.00 mol), N,N-diethylaniline (Et$_2$NPh) (268.61 g, 1.80 mol), and N,N-dimethylformamide (DMF) (300.00 g) were added to a reactor at room temperature and stirred at from 0 to 5° C. for 30 minutes. Next, methanesulfonyl chloride (MsCl) (6: X=Cl, R=Me) (160.37 g, 1.40 mol) was added dropwise to the reactor at an internal temperature of 10° C. or below. After the completion of the dropwise addition, the reaction mixture was heated to an internal temperature of from 60 to 65° C. and stirred for 8 hours. After lowering the internal temperature to 30° C., acetic acid (108.09 g) and water (500.00 g) were added to cause phase separation and the aqueous phase thus obtained was removed. Then, sodium hydrogen carbonate (25.00 g) and water (500.00 g) were added to the organic phase to wash the same, followed by phase separation and removal of the aqueous phase. The organic phase thus obtained was concentrated in a reduced pressure and the residue was subjected to distillation in a reduced pressure to obtain 2-chloropentane (5: X=Cl) (48.54 g, 0.46 mol) in a yield of 46.0%. 1-Chloropentane and 1-pentene, i.e., regioisomers of 2-chloropentane (5: X=Cl), was not observed in GC analysis. The spectrum data of the 2-chloropentane (5: X=Cl) obtained above were the same as those of the 2-chloropentane (5: X=Cl) obtained in Example 1.

Example 5A

Preparation of 4-methyl-5-nonanone (3)

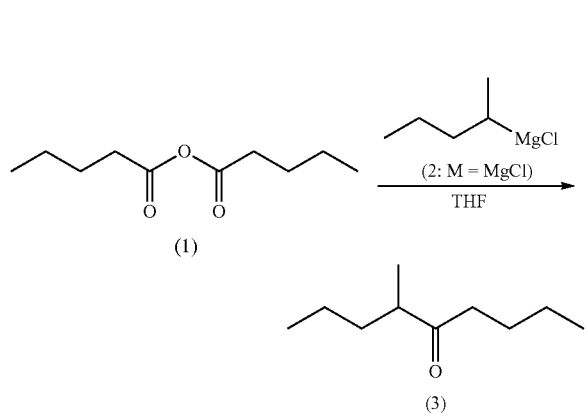

Magnesium (37.10 g, 1.53 gram atoms) and tetrahydrofuran (THF) (136.20 g) were added to a reactor at room temperature and stirred at from 60 to 65° C. for 40 minutes. After the stirring, 2-chloropentane (154.98 g, 1.45 mol) was added dropwise to the reactor at from 60 to 75° C. and the reaction mixture was stirred at from 75 to 80° C. for 2 hours to prepare 2-pentylmagnesium chloride (2: M=MgCl).

Then, tetrahydrofuran (540.06 g) and pentanoic anhydride (270.81 g, 1.53 mol) were added to another reactor and the whole amount of the 2-pentylmagnesium chloride (2: M=MgCl) obtained above was added dropwise at from −5 to 10° C. After the completion of the dropwise addition, the reaction mixture was stirred at from 0 to 10° C. for 3 hours. Then, acetic acid (114.55 g) and water (563.52 g) were added to the reaction mixture in the reactor to cause phase separation and the aqueous phase thus obtained was removed. An aqueous 25 wt % sodium hydroxide solution (319.88 g, 2.00 mol of sodium hydroxide) and water (872.40 g) were added to the organic phase in the reactor at room temperature and stirred for 60 minutes for neutralization. An organic phase and an aqueous phase (1693.25 g) containing sodium pentanoate (9: Y=Na) were obtained by phase separation. Subsequently, it was confirmed using a pH test strip that the aqueous phase containing sodium pentanoate (9: Y=Na) had a pH of 14.0. Next, acetic acid (4.15 g) and water (207.71 g) were added to the resulting organic phase to wash the same, followed by phase separation. The organic phase was concentrated in a reduced pressure and the residue was subjected to distillation in a reduced pressure to obtain 4-methyl-5-nonanone (3) (208.28 g, 1.32 mol, purity: 99.41%) in a yield of 90.8%.

The following is spectrum data of the 4-methyl-5-nonanone (3) thus prepared.

[Nuclear magnetic resonance spectrum] $^1$H-NMR (500 MHz, CDCl$_3$): δ=0.87 (3H, t, J=7.3 Hz), 0.89 (3H, t, J=7.3 Hz), 1.04 (3H, d, J=6.9 Hz), 1.14-1.66 (2H, m), 1.24-1.33 (4H, m), 1.53 (2H, tt, J=7.6, 7.6 Hz), 2.41 (2H, dt, J=2.7, 7.5 Hz), 2.51 (1H, tq, J=6.8, 6.8 Hz); $^{13}$C NMR (500 MHz, CDCl$_3$): δ=13.87, 14.09, 16.30, 20.46, 22.39, 25.78, 35.16, 40.82, 46.06, 215.11

[Mass spectrum] EI-Mass spectrum (70 eV): m/z 156 (M$^+$), 141, 127, 99, 85, 71, 57, 43, 29

[Infrared absorption spectrum] (NaCl): ν=2960, 2933, 2874, 1713, 1459, 1378

Example 5B

Recovery of Pentanoic Acid (8)

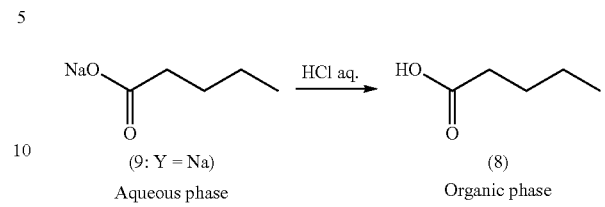

The aqueous phase (1693.25 g) containing sodium pentanoate (9: Y=Na) obtained in Example 5A was added to a reactor and an aqueous 20 wt % hydrochloric acid (389.19 g, 2.13 mol of hydrogen chloride) was added dropwise at from 10 to 20° C. After the completion of the dropwise addition, the reaction mixture was stirred at from 15 to 25° C. for one hour. The reaction mixture was left to stand. After pentanoic acid was liberated and the reaction mixture separated into an organic phase and an aqueous phase, the aqueous phase was removed by a phase separation to take up the organic phase containing the pentanoic acid (8). It was confirmed by a pH test strip that the aqueous phase had a pH of 1.0. The organic phase thus obtained was concentrated in a reduced pressure to obtain pentanoic acid (8) (132.67 g, 1.30 mol) in a yield of 89.3%.

The following is spectrum data of the pentanoic acid (8) thus recovered.

[Nuclear magnetic resonance spectrum] $^1$H-NMR (500 MHz, CDCl$_3$): δ=0.92 (3H, t, J=7.3 Hz), 1.37 (2H, tq, J=7.5, 7.5 Hz), 1.62 (2H, tt, J=7.6, 7.6 Hz), 2.35 (2H, t, J=7.5 Hz), 11.69 (1H, br, s); $^{13}$C-NMR (500 MHz, CDCl$_3$): δ=13.63, 22.15, 26.69, 33.82, 180.66

[Mass spectrum] EI-Mass spectrum (70 eV): m/z 101 (M$^+$-1), 87, 73, 60

[Infrared absorption spectrum] (NaCl): ν=2962, 2936, 2875, 2674, 1710, 1413, 1279, 1215, 940

Example 6

Preparation of Pentamoic Anhydride (1), Using the Recovered Pentanoic Acid (8)

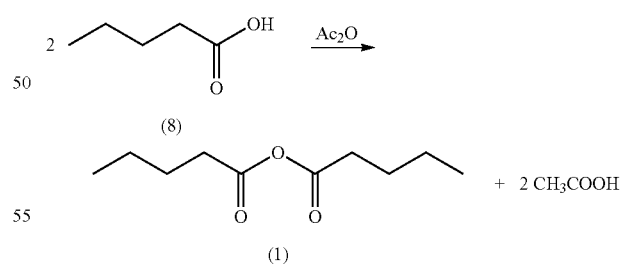

First, a distillation tower was connected to one of the ports of a reactor and a fractionating tower was connected to the outlet of the distillation tower. Further, a thermometer and a condenser were connected to the fractionating tower.

The pentanoic acid (8) (132.67 g, 1.30 mol) recovered in Example 5B and acetic anhydride (Ac$_2$O) (265.24 g, 2.60 mol) were added to the aforesaid reactor at room temperature. The fractionating tower was then closed and the mixture as stirred at an internal temperature of 150° C. and normal pressure for 30 minutes. Next, the fractionating tower was opened and acetic acid was subjected to distillation at an internal temperature of 150° C. and normal pressure, until an acetic acid content in the distillate containing at least acetic acid, acetic anhydride, and acetic pentanoic anhydride became 5.0%. Further, the pressure was reduced gradually to 70 mmHg at an internal temperature of 150° C. to distill acetic anhydride off. After the acetic, anhydride content in the distillate containing at least acetic anhydride, nentanol, acetic pentanoic anhydride, and pentanoic anhydride became 0.5%, the pressure was reduced to 5 mmHg to distill pentanoic anhydride (1) off. The internal temperature decreased to 130° C. at that time. The pentanoic anhydride (1) (214.12 g, 1.15 mol) was obtained in a yield of 88.5%.

The following is the spectrum data of the pentanoic anhydride (1) thus obtained.

[Nuclear magnetic resonance spectrum] $^1$H-NMR (500 MHz, CDCl$_3$): δ=0.92 (6H, t, J=7.3 Hz), 1.37 (4H, tq, J=7.5, 7.5 Hz), 1.63 (4H, tt, J=7.6, 7.6 Hz), 2.44 (4H, t, J=7.7 Hz); $^{13}$C-NMR (500 MHz, CDCl$_3$): δ=13.59, 21.95, 26.20, 34.93, 169.57

[Mass spectrum] EI-Mass spectrum (70 eV): m/z 187 (M$^+$+1), 144, 85, 57, 29

[Infrared absorption spectrum] (NaCl): ν=2961, 2936, 2875, 1818, 1750, 1467, 1413, 1036, 909

Example 7

Preparation of 4-methyl-5-nonanol (7)

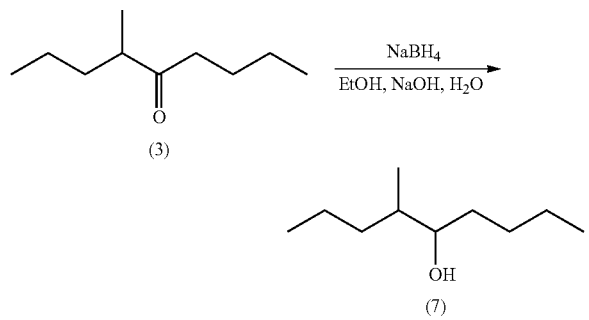

Sodium borohydride (NaBH$_4$) (11.77 g, 0.31 mol), ethanol (97.88 g), an aqueous 25 wt % sodium hydroxide solution (2.92 g, 0.018 mol of sodium hydroxide), and water (78.77 g) were added to a reactor at room temperature and 4-methyl-5-nonanone (3) (140.00 g, purity: 99.69%, 0.89 mol) was added dropwise at from 15 to 25° C. After the completion of the dropwise addition, the reaction mixture was stirred at from 30 to 35° C. for 10 hours and then phase-separated to obtain an organic phase. Acetic acid (10 g) and water (100 g) were added to the resulting organic phase to cause phase separation again. Subsequently, the organic phase was concentrated at a reduced pressure and the residue was subjected to distillation at a reduced pressure to obtain 4-methyl-5-nominal (7) (138.14 g, 0.82 mol purity: 99.75%, (syn-form):(anti-form)=50:50) in a yield of 97.5%.

The following is the spectrum data of the 4-methyl-5-nonanol (7) thus obtained.

[Nuclear magnetic resonance spectrum] $^1$H-NMR (500 MHz, CDCl$_3$): δ=0.86 (3H, t, J=6.9 Hz), 0.89 (3H, t, J=6.9 Hz), 0.90 (3H, t, J=7.1), 1.04-1.56 (12H, m), 3.40-3.50 (1H, m); $^{13}$C-NMR (500 MHz, CDCl$_3$): δ=13.48, 14.07, 14.30, 14.34, 15.18, 20.39, 20.44, 22.77, 22.79, 28.32, 28.45, 33.01, 34.10, 34.13, 35.58, 37.86, 38.52, 75.15, 76.02

[Mass spectrum] EI-Mass spectrum (70 eV): m/z 157 (M$^+$−1), 140, 101, 87, 69, 55, 41

[Infrared absorption spectrum] (NaCl): ν=3363, 2958, 2931, 2873, 1467, 1379, 1012, 976

The invention claimed is:

1. A process for preparing 4-methyl-5-nonanone of the following formula (3):

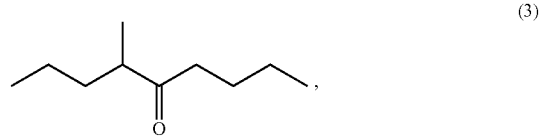

the process comprising at least a step of
subjecting pentanoic anhydride of the following formula (1):

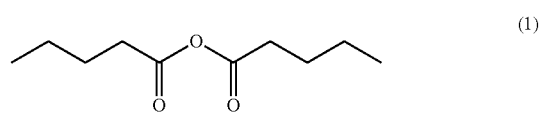

and a 2-pentyl nucleophilic reagent of the following general formula (2):

$$CH_3CH_2CH_2CH(CH_3)M \qquad (2)$$

in which M represents Li, MgZ$^1$, or ZnZ$^1$, wherein Z$^1$ represents a halogen atom or a 2-pentyl group,
to a nucleophilic substitution reaction to produce 4-methyl-5-nonanone (3).

2. The process according to claim 1, further comprising subjecting 2-pentanol of the following formula (4):

and a halogenating agent to a halogenation reaction to produce a 2-halopentane compound of the following general formula (5):

in which X represents a halogen atom; and
preparing the aforesaid 2-pentyl nucleophilic reagent (2) from the aforesaid 2-halopentane compound (5).

3. The process according to claim 2, wherein the halogenating agent is a sulfonyl halide compound of the following formula (6):

$$XSO_2R \qquad (6)$$

in which X represents a halogen atom, wherein R represents a monovalent hydrocarbon group having from 1 to 7 carbon atoms, and the halogenation reaction is carried out in the presence of a basic compound.

4. The process according to claim 1, further comprising during or after the aforesaid nucleophilic substitution reaction, recovering pentanoic acid which was by-produced in the nucleophilic substitution reaction.

5. The process according to claim 4, further comprising subjecting the recovered pentanoic acid to a condensation reaction to produce pentanoic anhydride (1).

6. The process according to claim 5, wherein the obtained pentanoic anhydride (1) is used in the nucleophilic substitution reaction.

7. The process according to claim 5, further comprising repeating the nucleophilic substitution reaction with use of the obtained pentanoic anhydride (1) as a raw material for the nucleophilic substitution reaction.

8. A process for preparing 4-methyl-5-nonanol of the following formula (7):

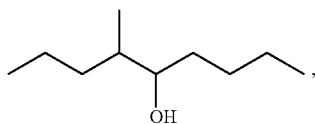
(7)

the process comprising at least steps of
preparing 4-methyl-5-nonanone (3) according to claim 1; and
subjecting the obtained 4-methyl-5-nonanone (3) and a reducing agent to a reduction reaction to produce 4-methyl-5-nonanol (7).

9. The process according to claim 2, further comprising during or after the aforesaid nucleophilic substitution reaction, recovering pentanoic acid which was by-produced in the nucleophilic substitution reaction.

10. The process according to claim 9, further comprising subjecting the recovered pentanoic acid to a condensation reaction to produce pentanoic anhydride (1).

11. The process according to claim 10, wherein the obtained pentanoic anhydride (1) is used in the nucleophilic substitution reaction.

12. The process according to claim 10, further comprising repeating the nucleophilic substitution reaction with use of the obtained pentanoic anhydride (1) as a raw material for the nucleophilic substitution reaction.

13. The process according to claim 3, further comprising during or after the aforesaid nucleophilic substitution reaction, recovering pentanoic acid which was by-produced in the nucleophilic substitution reaction.

14. The process according to claim 13, further comprising subjecting the recovered pentanoic acid to a condensation reaction to produce pentanoic anhydride (1).

15. The process according to claim 14, wherein the obtained pentanoic anhydride (1) is used in the nucleophilic substitution reaction.

16. The process according to claim 14, further comprising repeating the nucleophilic substitution reaction with use of the obtained pentanoic anhydride (1) as a raw material for the nucleophilic substitution reaction.

* * * * *

UNITED STATES PATENT AND TRADEMARK OFFICE
CERTIFICATE OF CORRECTION

PATENT NO. : 10,882,806 B2  
APPLICATION NO. : 16/722138  
DATED : January 5, 2021  
INVENTOR(S) : Miyake et al.

Page 1 of 1

It is certified that error appears in the above-identified patent and that said Letters Patent is hereby corrected as shown below:

On the Title Page

(56) References Cited, OTHER PUBLICATIONS, Column 2, Line 18, Ahn et al. cite:  
Please correct "208 (1994)." to read -- 206 (1994). --

In the Specification

Column 11, Line 15:  
Please correct "2.5°" to read -- 25° --

Signed and Sealed this  
Seventeenth Day of August, 2021

Drew Hirshfeld  
*Performing the Functions and Duties of the*  
*Under Secretary of Commerce for Intellectual Property and*  
*Director of the United States Patent and Trademark Office*